US00PP19004P2

(12) United States Plant Patent
Zary

(10) Patent No.: US PP19,004 P2
(45) Date of Patent: Jul. 8, 2008

(54) HYBRID TEA ROSE PLANT NAMED 'JACGODDE'

(50) Latin Name: *Rosa hybrida*
Varietal Denomination: JACgodde

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/585,432

(22) Filed: Oct. 23, 2006

(51) Int. Cl.
*A01H 5/00* (2006.01)

(52) U.S. Cl. ..... Plt./130
(58) Field of Classification Search ..... Plt./130
See application file for complete search history.

*Primary Examiner*—Kent Bell
*Assistant Examiner*—S. B. McCormick-Ewoldt
(74) *Attorney, Agent, or Firm*—Klarquist Sparkman, LLP

(57) ABSTRACT

Hybrid tea rose plant having a strong anise fragrance; complex, attractive apricot and yellow-pink flower color; vigorous, upright, well-balanced plant habit; strong foliage resistant to most diseases; strong cutting stems; and good high centered flower form.

1 Drawing Sheet

Figure 1:
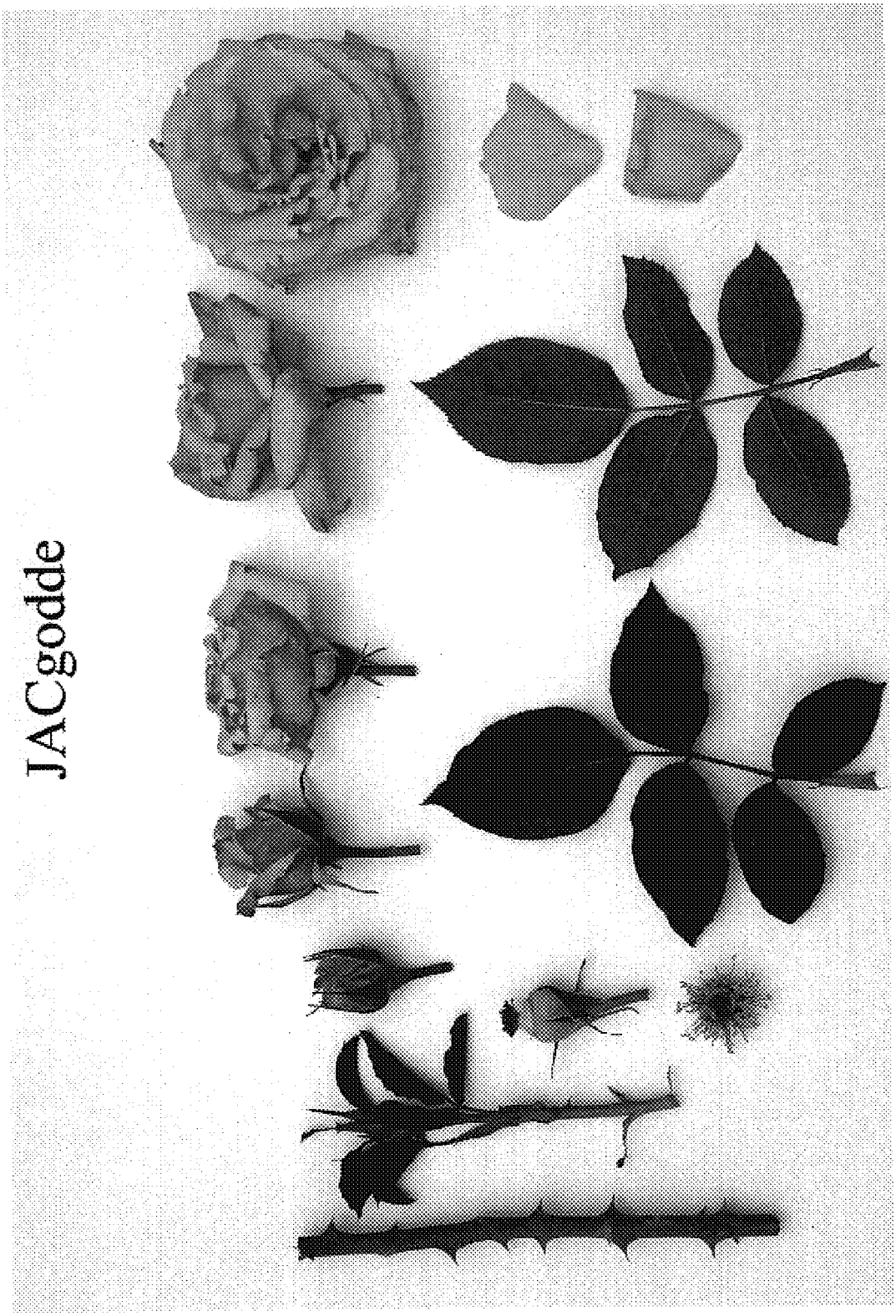

Genus and species: *Rosa hybrida.*
Variety denomination: 'JACgodde'.

ORIGIN OF THE INVENTION

The present invention relates to a new and distinct variety of a hybrid tea rose plant named 'JACgodde' which was originated by me by crossing an unnamed orange hybrid tea seedling (not patented) (unnamed seedling orange-pink× unnamed yellow hybrid tea seedling) with the variety 'JACdash' (U.S. Plant Pat. No. 7,659).

BACKGROUND OF THE INVENTION

The primary objective of this breeding was to produce a new hybrid tea rose variety having the disease resistant foliage and vigor of the female parent combined with the good flower form, the fragrance and long cutting stems of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Strong anise fragrance.
2. Complex, attractive apricot and yellow-pink flower color.
3. Vigorous, upright, well-balanced plant habit.
4. Strong foliage resistant to most diseases.
5. Strong cutting stems.
6. Good high centered flower form.

Asexual reproduction of this new variety by cuttings and budding, as performed at Wasco and Somis, Calif., shows that the foregoing and all other characteristics and distinctions come true to form and are established and transmitted through succeeding propagations.

Comparison with Parents

The female parent, an orange hybrid tea seedling, differs from 'JACgodde' in flower color and in its light, spicy fragrance. The male parent, a yellow hybrid tea, differs from 'JACgodde' in having a lighter yellow flower color.

Comparison with Similar Variety

'JACgodde' differs from all hybrid teas by its unusual combination of fragrance, disease resistance, unusual flower color and vigor.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—Unnamed orange hybrid tea seedling (not patented) (unnamed orange-pink seedling× unnamed yellow hybrid tea seedling).
*Pollen parent.*—'JACdash', (U.S. Plant Pat. No. 7,659).

FLOWER

Observations made from January 2005 to July 2006 from plants commencing at two years of age grown in a garden environment at Somis, Calif.

Blooming habit: Continuous.
Bud:
*Size.*—About 45 cm long and 25 cm in diameter when the petals start to unfurl.

*Form.*—The bud form is long, pointed ovoid.

*Color.*—When sepals first divide, bud color is a blend of Yellow-Orange Group 16A, Orange Group 24B and Red Group 43C. When half blown, the upper sides of the petals are mainly Yellow-Orange Group 16A with Red Group 47C on margins of outer petals and the lower sides of the petals are mainly Yellow-Orange Group 16A with Red Group 47C more dominant than on upper sides.

*Sepals.*—Color: Upper surface: Green Group 138C. Lower surface: Green Group 138B, but often with an overlay of Greyed-Purple Group 183B. Length: 30–35 mm. Width: 11–12 mm. Shape: Subulate. Surface texture: Upper; hoary; Lower: smooth. There are three lightly to normally appendaged sepals. There are two unappendaged sepals with hairy edges.

*Receptacle.*—Color: Green Group 138B. Shape: Funnel. Size: Medium, about 10–11 mm wide×7–8 mm long. Surface: Smooth.

*Peduncle.*—Length: Short, averaging about 40–45 mm. Surface: Smooth. Color: Green Group 138B, but often with Greyed-Red Group 178C overlay in areas exposed to bright sunlight. Strength: Stiff, erect.

Bloom:

*Size.*—Large. Average open diameter is about 10–12 cm.

*Borne.*—Singly.

*Stems.*—Strength: Strong. Average length is about 40–50 cm with a diameter of 5–7 mm.

*Form.*—When first open: High centered. Permanence: All petals curl.

*Petalage.*—Number of petals under normal conditions: 30–35.

*Color.*—The upper sides of the petals are Yellow-Orange Group 16A with outer petals having slight tipping of Red Group 47C. The reverse sides of the petals are Yellow-Orange Group 23C with occasional variegations of Red Group 42C. The bases of the reverse side of the petals have a Yellow-Orange Group 14B spot. The major color on the upper sides is Yellow-Orange Group 21B.

*Discoloration.*—The general tonality at the end of the first day: Two-thirds Yellow-Orange Group 16A, one-third Red Group 47C. At the end of the third day: Four-fifths Yellow-Orange Group 16A, one-fifth Red Group 47C. Further aging: Fades to Yellow-Orange 16C by day seven then petals drop by day nine.

*Fragrance.*—Strong, anise.

Petals:

*Texture.*—Thick.

*Shape.*—Obcordate.

*Surface.*—Smooth.

*Margin.*—Crenate. Apex Shape: Obcordate. Base Shape: Oblique.

*Form.*—Moderately quilled.

*Arrangement.*—Imbricated.

*Petaloids.*—Number: 3 to 5. Size: 3–8 mm long×1–5 mm wide. Color: Upper: Yellow-Orange Group 16A. Lower: Yellow-Orange Group 23C.

*Persistence.*—Petals drop cleanly.

*Lastingness.*—On the plant: Fair (about 5 days). As a cut flower: Fair (about 5 days).

Reproductive parts:

*Stamens.*—Number: 90–95. Length: 13–14 mm. Anthers: Length: 3 mm. Color: Yellow-Orange Group 16A. Filaments: Color: Red Group 46C. Length: 10–11 mm Pollen: Color: Yellow-Orange Group 22A.

*Pistils.*—Number: 55–60. Length: 5 mm. Styles: Color: Red-Purple Group 59A. Length: 4 mm. Stigmas: Color: Greyed-Yellow Group 161D. Length: 1 mm.

*Hips.*—None observed.

PLANT

*Form.*—Bush.

*Growth.*—Vigorous, upright, branching.

*Age at maturity.*—Two years.

*Mature plant.*—Height: 180 cm. Width: 120 cm.

*Rootstock.*—Own root or Dr. Huey (not patented). Grows well on its own roots.

Foliage: Number of leaflets on normal mid-stem leaves: 5 or 7.

*Size.*—Large. About 13 cm long×10 cm wide.

*Quantity.*—Abundant.

*Color.*—New foliage: Upper side: Greyed-Purple Group 187A. Lower surface: Greyed-Purple Group 183A. Old foliage: Upper side: Green Group 139A. Lower side: Green Group 147B.

Leaflets:

*Size.*—About 50–55 mm long×30–33 mm wide.

*Shape.*—Oval.

*Base shape.*—Oblique to rounded.

*Apex shape.*—Acuminate.

*Texture.*—Leathery.

*Edge.*—Serrated.

*Serrations.*—Single, small.

*Petiole.*—Color: Yellow-Green Group 146C.

*Petiole rachis.*—Color: Yellow-Green Group 146C. Underside: Rough with prickles.

*Auricles.*—None.

*Stipules.*—Length: 16–18 mm, serrated.

*Disease resistance.*—Resistant to rust, mildew and blackspot under normal growing conditions.

*Pest resistance.*—Not observed.

*Vein color.*—Yellow-Green Group 146C.

*Venation pattern.*—Reticulate.

Wood:

*New wood.*—Color: Greyed-Purple Group 183D. Bark: Smooth.

*Old wood.*—Color: Green Group 137C. Bark: Smooth.

Prickles:

*Quantity.*—On main canes from base: Ordinary (15–18 per 15 cm of stem). On laterals from main canes: Ordinary (12–15 per 15 cm of stem).

*Form.*—Hooked downward.

*Length.*—8–10 mm.

*Color when young.*—Greyed-Purple Group 183D.

*Color when mature.*—Greyed-Yellow Group 160B.

Small prickles:

*Quantity.*—On main stalks: None. On laterals: None.

Winter Hardiness: Hardy to Zone 5.

I claim:

1. A new and distinct variety of rose plant of the hybrid tea class, substantially as herein shown and described, characterized particularly by its strong anise fragrance; complex, attractive apricot and yellow-pink flower color; vigorous, upright, well-balanced plant habit; strong foliage resistant to most diseases; strong cutting stems; and good high centered flower form.

* * * * *

UNITED STATES PATENT AND TRADEMARK OFFICE

CERTIFICATE OF CORRECTION

PATENT NO. : PP 19,004 P2
APPLICATION NO. : 11/585432
DATED : July 8, 2008
INVENTOR(S) : Keith W. Zary It is certified that error appears in the above-identified patent and that said Letters Patent is hereby corrected as shown below:

Column 3, line 14, “Upper; hoary;” should read --Upper: hoary;--.

Column 3, line 54, “Texture.-Thick.” should be deleted.

Column 4, line 22, “Lower surface:” should read --Lower side:--.

Signed and Sealed this

Twenty-sixth Day of May, 2009

JOHN DOLL
*Acting Director of the United States Patent and Trademark Office*